United States Patent [19]

Ciavattoni et al.

[11] 4,168,633

[45] Sep. 25, 1979

[54] PANORAMIC DENTAL X-RAY MACHINE BASE EXCURSION DRIVE ASSEMBLY

[75] Inventors: Anthony Ciavattoni, Staten Island, N.Y.; Josef Ujvary, Kingston; Robert H. Cushman, Princeton, both of N.J.

[73] Assignee: Pennwalt Corporation, Philadelphia, Pa.

[21] Appl. No.: 856,423

[22] Filed: Dec. 1, 1977

[51] Int. Cl.² .............................................. F16H 33/10
[52] U.S. Cl. ................................... 74/86; 250/439 P; 297/349
[58] Field of Search .................... 74/86; 297/349, 330; 32/22; 250/439 P; 64/30 R

[56] References Cited

U.S. PATENT DOCUMENTS

| 1,168,071 | 1/1916 | Holzbaur | 297/349 |
| 1,337,059 | 4/1920 | Fisher | 297/349 |
| 2,613,726 | 10/1932 | Paatero | 297/349 |
| 2,684,446 | 7/1954 | Paatero | 250/439 P |
| 3,481,160 | 12/1969 | Georgi | 64/30 R |
| 3,743,832 | 7/1973 | Wright | 250/439 P |

*Primary Examiner*—Samuel Scott
*Assistant Examiner*—Wesley S. Ratliff, Jr.

[57] ABSTRACT

Excursion mechanism for rotating a large rotating disc member having a column upstanding therefrom at an outer portion thereof, the column being permanently affixed thereto. The column supports an X-ray source and camera for radiographing a patient's dental arch area. The column circularly orbits about the patient seated in a patient chair which rests on a stationary platform disposed above the large rotating disc member. A sprocket is rotatably mounted on the rotating disc member. A belt articulates between the sprocket and the stationary patient platform such that rotation of the sprocket through external motor means causes the large rotating disc member and column to orbit the patient.

10 Claims, 5 Drawing Figures

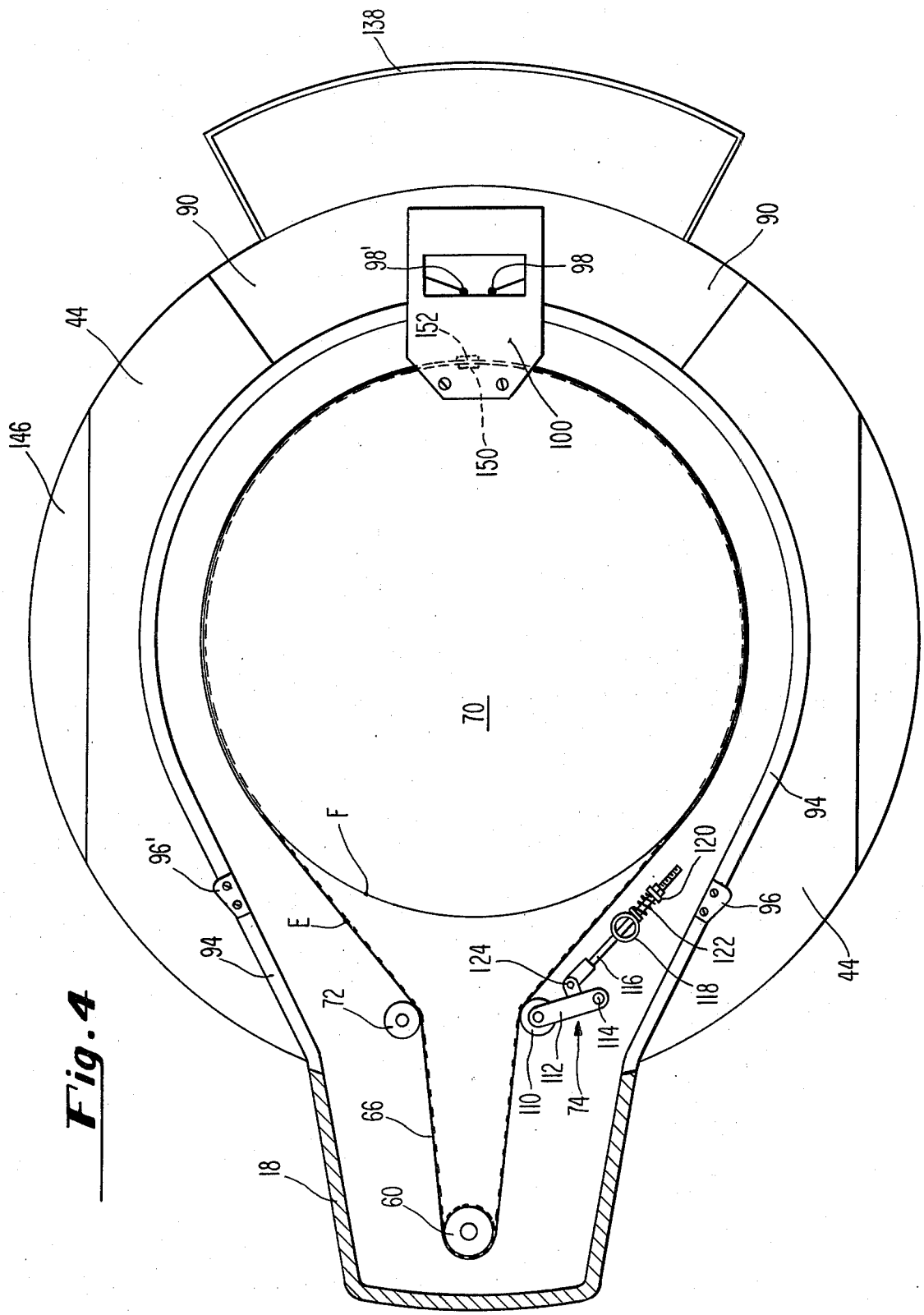

PANORAMIC DENTAL X-RAY MACHINE BASE EXCURSION DRIVE ASSEMBLY

STATEMENT OF THE INVENTION

The present invention relates to X-ray apparatus for taking panoramic radiographs of dental arch and temporomandibular joint areas and more particularly concerns apparatus which causes a column carrying an X-ray tubehead and camera to orbit about a patient in a smooth and vibrationless manner.

BRIEF DESCRIPTION OF THE DRAWINGS

FIG. 4 is a plan view, partially in section, of the excursion mechanism with portions removed for clarity.

DETAILED DESCRIPTION OF THE INVENTION

Figures 1, 5:
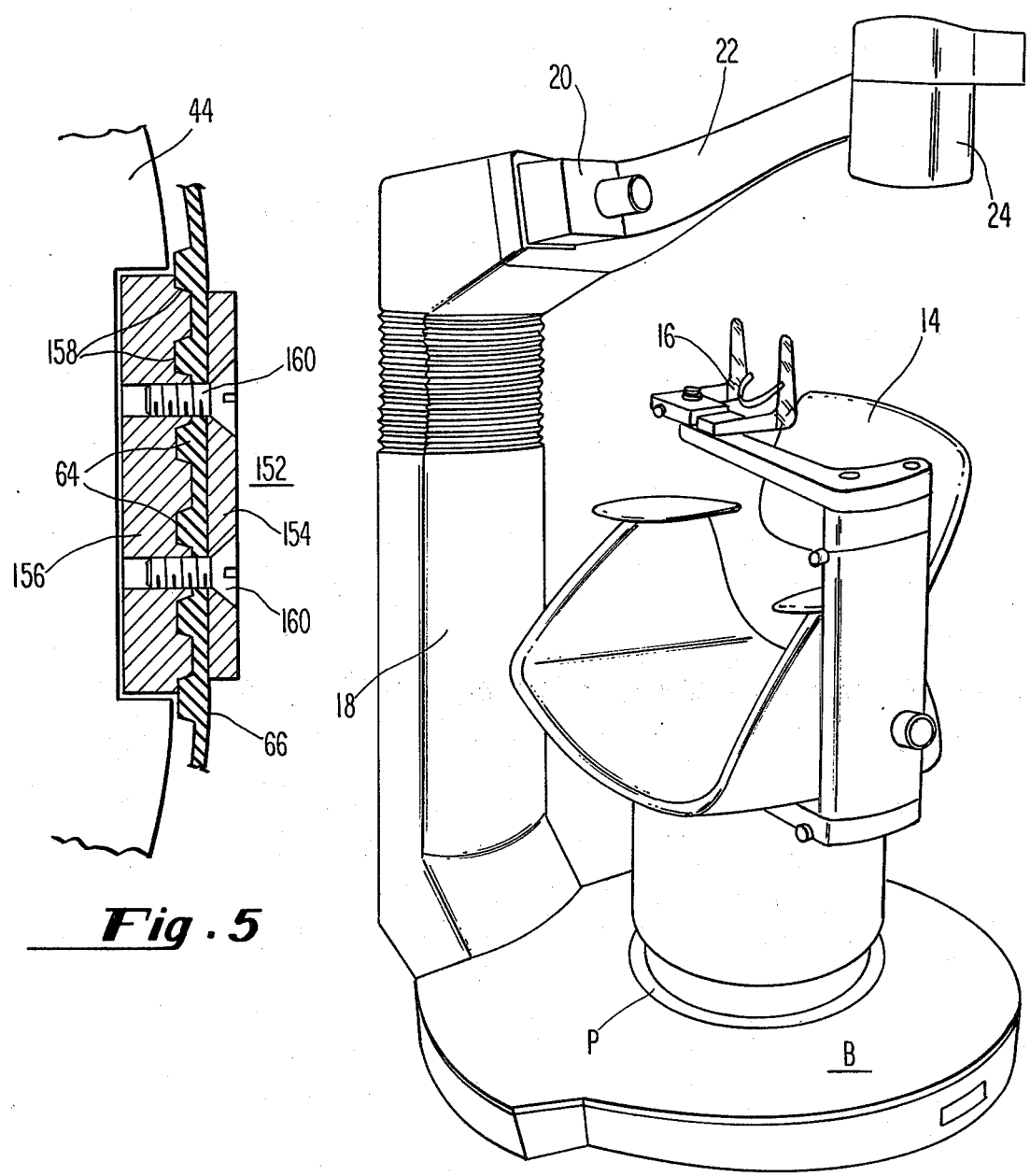
FIG. 1 is a perspective view of dental X-ray apparatus embodying the invention.
FIG. 5 is a sectional view of the belt-fastening means used in the excursion mechanism.

Referring to FIG. 1 of the drawings, the panoramic X-ray apparatus comprises a base B which supports and partially houses the excursion mechanism of the invention. A stationary platform P is disposed generally centrally of the base B, the platform carrying a patient chair 14 including means 16 for supporting the chin and head of a patient. A column 18 is caused to rotate around chair 14 by means of the excursion mechanism. Column 18 includes a tubehead 20, a camera supporting arm 22 and a camera 24 which includes the usual film holding means.

Figure 2:
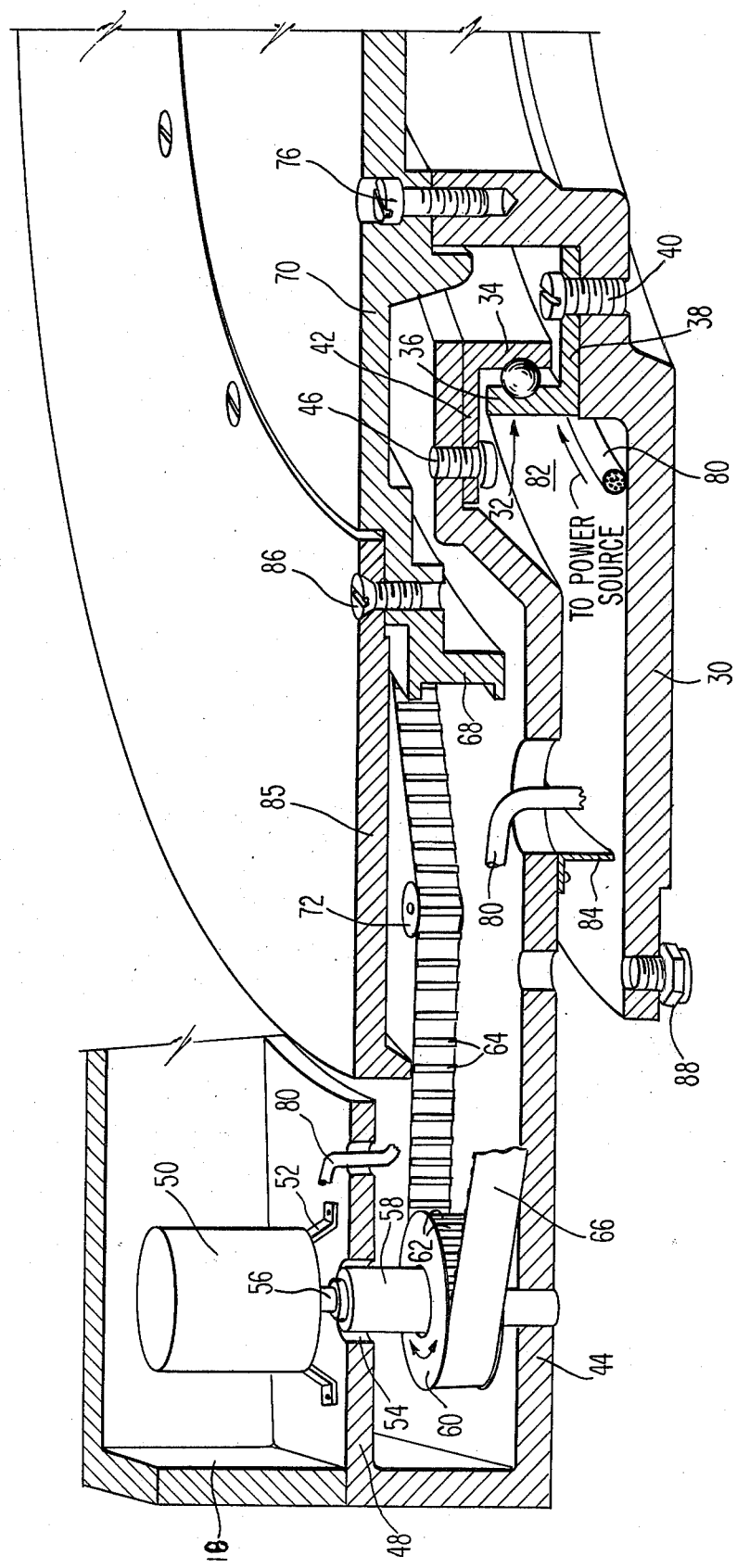
FIG. 2 is a cutaway perspective view of a portion of the base and excursion mechanism of the embodiment shown in FIG. 1.

FIG. 2, a base plate 30, preferably an aluminum casting, carries a circular flange mounted bearing 32 having an inner race 34 and an outer race 36. Outer race 36 includes a lower flange 38 which is secured to base plate 30 by circumferentially spaced screws 40. Similarly, upper flange 42 of inner race 34 carries rotating disc 44. Upper flange 42 and rotating disc 44 rotate as a unit and are held together by means of circumferentially spaced shoulder screws 46.

Rotating disc 44 carries column 18 which is provided with a horizontal plate member 48, upon which is mounted a synchronous step motor 50 by means of brackets 52. An opening 54 is provided in horizontal plate 48 through which shaft 56 of motor 50 communicates with conventional electromagnetic slip clutch 58. Clutch 58 serves to couple shaft 56 with sprocket 60 which is rotatably mounted to rotating disc 44. Sprocket 60 is provided with teeth 62 which coact with spaced projections 64 on a belt 66. The belt is accommodated within an annulus 68 provided around stationary platform 70 which supports the patient chair 14.

It should be emphasized that belt 66 does not rotate around platform 70. Belt 66 is held immovable against annulus 68 at that portion of the annulus farthest removed from sprocket 60 by means to be described more fully hereinafter. To further clarify, any given point on belt 66, such as point E (FIG. 4) for example, will always contact a specified point, and no other point, on annulus 68 provided around platform 70, such as point F, regardless of the direction of rotation of rotating disc 44. Belt 66 provides the means therefore for translating the rotation of sprocket 60 into orbital rotation of rotating disc 44 and column 18.

A fixed idler pulley 72 is rotatably mounted to rotating disc 44, while an adjustable idler pulley assembly 74 (FIG. 4) is pivotally mounted to rotating disc 44, both pulleys cooperating to maintain proper tension of belt 66 against sprocket 60 and annulus 68. Platform 70 is fixedly secured to base plate 30 by screws 76.

A flexible electric cable 80 passes up through column 18 for connecting the power source to the X-ray source and camera, and to the motor (not shown) which elevates or lowers the tubehead assembly in column 18. The cable is also connected to motor 50, slip clutch 58, and a microswitch assembly to be later described. In order to insure unimpeded vertical movement of the tubehead assembly and the orbiting of column 18, cable 80 will be provided with a sufficient length. To that end, a space 82 is provided above base plate 30 to permit coiling and uncoiling of cable 80 during movement of the tubehead and column. A cable control band 84 is mounted to an underside portion of rotating disc 44 for restricting cable 80 within space 82.

A removable cover plate or step plate 85, suitably an aluminum casting, protects the excursion mechanism as well as affording means upon which the patient may step and rest his feet. Step plate 85 is removably attached to stationary platform 70 by screws 86. Leveling screws 88 are provided in base plate 30.

Figure 3:
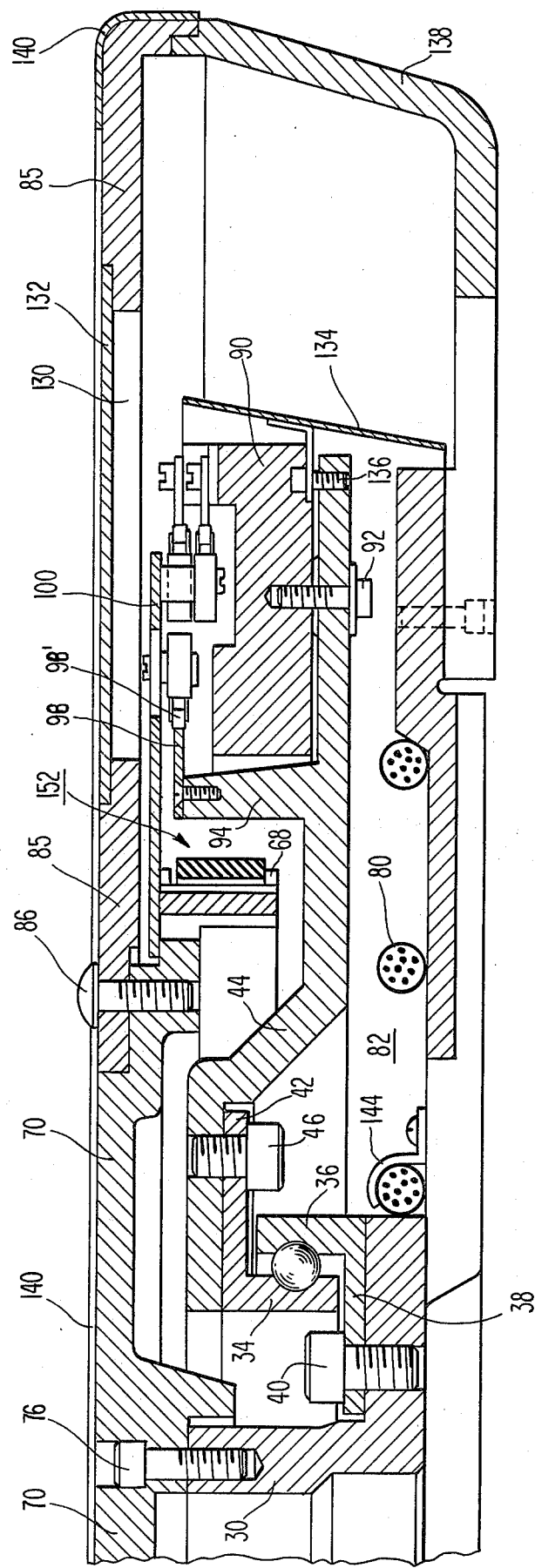
FIG. 3 is a sectional view of another portion of the base and excursion mechanism.

For a better understanding of the invention, reference should now be made to FIGS. 3 and 4 wherein a balancing weight 90, suitably cast iron, is shown seated on an outer portion of rotating disc 44, the weight 90 being positioned in counterbalancing relation to column 18. Screws 92 maintain balance weight 90 in a fixed position on rotating disc 44. An annular ring 94 upstands from rotating disc 44 and carries a pair of cams 96 and 96' which respectively actuate microswitches 98 and 98' to limit the total excursion of rotating disc 44 to about 240°. Microswitches 98 and 98' are carried on a switch plate 100 mounted on stationary platform 70. More specifically, when rotating disc 44 moves in a counterclockwise direction, switch 98 will be actuated by cam 96 to open the circuit to motor 50. Conversely, cam 96' actuates limit switch 98' when rotating disc 44 moves in a clockwise direction to open the circuit to motor 50. Cams 96 and 96' are so positioned that column 18 and rotating disc 44 are permitted about 240° of rotation in either direction. Circuitry for the cam-microswitch arrangement is conventional and are not detailed herein.

Adjustable idler pulley assembly 74 comprises an idler wheel 110 rotatable on arm 112 which is pivotally mounted to rotating disc 44 by screw 114. A holder 116 is slidably insertable through a nut 118 which is fixedly secured to rotating disc 44. Thus, idler wheel 110 will be displaced inwardly to increase tension on belt 66 when screw 120 is tightened against compression spring 122 to cause arm 112 to pivot clockwise on screw 114 by means of pivot pin 124.

Step plate 85 is provided with a recess 130 for receiving a removable access plate 132 for easy access to switch plate 100.

A skirt 134 extends around rotating disc 44, and is mounted thereto by screws 136 while a step plate support member 138 is bolted to base plate 30. A step plate cover 140, preferably rubber or vinyl, is fitted over the step plate.

A clamp 144 may be employed to secure cable 80 against base plate 30.

Rotating disc 44 may be provided with removable wings 146 to enable passage of the X-ray machine through restricted openings.

Annulus 68 of stationary platform 70 has a cut-out area, or notched recess 150 for receiving a belt-fastening assembly 152 therewithin (FIG. 5) comprising an outer plate 154 and an inner plate 156 which includes grooves 158 for accepting projections 64 of belt 66. The plates 154 and 156 are secured together by screws 160.

In the operation of the excursion mechanism, any rotary motion of shaft 56 of motor 50 will not be coupled to sprocket 60 until sufficient voltage is supplied to the coils of clutch 58. That is, the clutch will be permitted to "slip" until actuated. However, once actuated by a sufficient voltage, rotation of sprocket 60 will be effected. Since belt 66 is held fast against annulus 68 in the vicinity where belt-fastening assembly 152 engages notched recess 150 provided in stationary platform 70, rotation of the sprocket causes column 18 and rotating disc 44 to orbit around the stationary patient platform. Thus, belt 66 will translate the rotational movement of sprocket 60 into a clockwise or counterclockwise excursion of the column depending upon the direction of rotation of the sprocket. More specifically, rotation of sprocket 60 in a clockwise direction causes column 18 and rotating disc 44 to orbit in an opposite direction, and vice-versa.

Reversing the direction of rotation of shaft 56 of motor 50, and circuitry supplying the necessary voltage to actuate slip clutch 58 is well known. For the purposes of this invention, step motor 50 is geared down by conventional means to permit 1.83 rpm of the column and rotating disc.

We claim:

1. Excursion mechanism for driving a column in a circular path around a patient for taking panoramic X-ray photographs of dental arch and temporomandibular joint areas of said patient, said column carrying
    a tubeholder containing an X-ray source; and
    film holder means for holding film to be activated by said X-ray source, said excursion mechanism comprising
    (a) a base member,
    (b) bearing means including an outer race and an inner race, said outer race affixed concentrically about an upper portion of said base member,
    (c) a large rotating disc member disposed above said base member, said inner race affixed centrally to an underside portion of said rotating disc for rotation with said inner race, said base member and said bearing means and said rotating disc being in concentric alignment,
    (d) a stationary platform concentric with and secured to said base member, said platform being disposed above said rotating disc and centrally thereof,
    (e) a column upstanding from said rotating disc at an outer portion thereof, said column defining an enclosure,
    (f) a sprocket rotatably mounted on said rotating disc at an area defined by said enclosure, said sprocket having teeth forming alternate projections and depressions,
    (g) means mounted within said column for rotating said sprocket, and
    (h) means articulating between said sprocket and said stationary platform to translate rotational motion of said sprocket into orbital movement of said rotating disc and column.

2. The mechanism according to claim 1 wherein said means mounted within said column for rotating said sprocket is a synchronous step motor having a shaft rotating therefrom.

3. The mechanism according to claim 2 wherein a slip clutch is interposed between said motor and said sprocket for coupling rotation of said motor shaft to said sprocket.

4. The mechanism according to claim 1 wherein said platform is provided with an annulus adjacent its upper portion.

5. The mechanism according to claim 4 wherein said means articulating between said sprocket and said annulus is a belt, said belt having uniformly spaced projections thereon which correspondingly engage said depressions in said sprocket.

6. The mechanism according to claim 5 wherein belt tensioning means are mounted on said rotating disc, said belt tensioning means including
    a fixed idler pulley rotatably mounted on said rotating disc to contact said belt between said sprocket and said annulus,
    an adjustable idler pulley pivotally mounted on said rotating disc in cooperating relationship to said fixed idler pulley, said adjustable idler pulley controlling degree of tension of said belt against said sprocket and said annulus of said stationary platform.

7. The mechanism according to claim 6 wherein said annulus is provided with a recessed notch at a point farthest removed from said column,
    belt-fastening means for rendering said belt continuous, said belt-fastening means engaging said recessed notch and remaining secure within said notch upon rotation of said rotating disc and column.

8. The mechanism according to claim 7 wherein said rotating disc carries an upstanding annular ring disposed outwardly said annulus of said stationary platform and generally concentric therewith,
    cam means provided on said ring,
    a switch plate mounted on said stationary platform above said recessed notch and belt-fastening means,
    means affixed to said switch plate responsive to said cam means for limiting travel of said rotating disc and column in either a clockwise or counterclockwise direction.

9. The mechanism according to claim 7 wherein a balance weight is affixed to said rotating disc at an outer portion thereof in counterbalancing relationship to said column.

10. In a dental X-ray machine having a column including a tubeholder containing an X-ray source and film cassette therefore, said column adapted for orbital movement about a seated patient for taking panoramic X-ray photographs of a dental arch area of said patient, the combination therewith comprising the improvement of an excursion mechanism capable of providing about 240° of travel to said column, said excursion mechanism comprising,
    (a) a circular base member,
    (b) bearing means including an outer race and an inner race, said outer race affixed concentrically about an upper portion of said base member, (c) a large rotating disc member disposed above said base member, said inner race affixed centrally to an underside portion of said rotating disc for rotation upon said inner race, said base member and said bearing means and said rotating disc being in concentric alignment, (d) a stationary platform concentric with and secured to said base member, said platform being disposed above said rotating disc and inwardly centrally thereof, (e) a column upstanding from said rotating disc at an outer portion thereof, said column defining an enclosure, (f) a sprocket rotatably mounted on said rotating disc at an area defined by said enclosure, said sprocket having teeth forming alternate projections and depressions, (g) means mounted within said column for rotating said sprocket, and (h) means articulating between said sprocket and said stationary platform to translate rotational motion of said sprocket into orbital movement of said rotating disc and column.

* * * * *